(12) United States Patent
Wyslucha et al.

(10) Patent No.: US 9,918,795 B2
(45) Date of Patent: Mar. 20, 2018

(54) INSTRUMENT HOLDER

(71) Applicant: MAQUET GMBH, Rastatt (DE)

(72) Inventors: Ulrich Wyslucha, Weingarten (DE); Stefan Peter, Rastatt (DE)

(73) Assignee: Maquet GMBH, Rastatt (DE)

( * ) Notice: Subject to any disclaimer, the term of this patent is extended or adjusted under 35 U.S.C. 154(b) by 66 days.

(21) Appl. No.: 14/648,797

(22) PCT Filed: Dec. 3, 2013

(86) PCT No.: PCT/EP2013/075332
§ 371 (c)(1),
(2) Date: Jun. 1, 2015

(87) PCT Pub. No.: WO2014/095336
PCT Pub. Date: Jun. 26, 2014

(65) Prior Publication Data
US 2015/0297304 A1    Oct. 22, 2015

(30) Foreign Application Priority Data

Dec. 20, 2012  (DE) .......................... 10 2012 112 712

(51) Int. Cl.
*A61B 19/00*     (2006.01)
*F16B 2/06*      (2006.01)
(Continued)

(52) U.S. Cl.
CPC .............. *A61B 19/26* (2013.01); *A61B 90/50* (2016.02); *A61B 90/57* (2016.02); *F16B 2/065* (2013.01);
(Continued)

(58) Field of Classification Search
CPC ..... Y10T 403/32254; Y10T 403/32262; Y10T 403/32286; Y10T 403/32319;
(Continued)

(56) References Cited

U.S. PATENT DOCUMENTS 3,037,230 A  *  6/1962  Strand ................... A47L 13/252
                                                     15/143.1
3,419,295 A     12/1968 Small
(Continued)

FOREIGN PATENT DOCUMENTS

CN    101849132 A    9/2010
CN    102462533 A    5/2012
(Continued)

OTHER PUBLICATIONS

International Search Report for PCT/EP2013/075332 dated Apr. 14, 2014.
(Continued)

*Primary Examiner* — Ingrid M Weinhold

(57) ABSTRACT

An instrument holder is described for mounting a medical instrument on a joint arm, comprising a body, a holder for holding the medical instrument on the body, and a coupling element for attaching the body to the joint arm. The holder comprises a threaded shank provided with an external thread, a receiving disc and a locking element provided with an internal thread. The receiving disc has a through-hole, by which the receiving disc can be put on the threaded shank and is rotatable about the threaded shank.

11 Claims, 5 Drawing Sheets

(51) Int. Cl.
*F16M 13/02* (2006.01)
*A61B 90/57* (2016.01)
*A61B 90/50* (2016.01)
*A61B 17/00* (2006.01)

(52) U.S. Cl.
CPC . *F16M 13/022* (2013.01); *A61B 2017/00477* (2013.01)

(58) Field of Classification Search
CPC ..... Y10T 403/32368; Y10T 403/32401; Y10T 403/32418; Y10T 403/32426; Y10T 403/32442; Y10T 403/32451; Y10T 403/32459; F16M 13/022; A47J 45/07; A47J 45/071; A47J 45/075; A47J 45/077; A61B 90/50; A61B 17/02; A61B 2017/00477; A61B 17/0206; A61B 19/26; A61B 90/57; F16B 2/065
USPC ....... 600/201, 204, 210, 213, 215, 226–230, 600/234; 248/284.1, 276.1, 316.6; 16/110.1, 422, 423, 426, 428
See application file for complete search history.

(56) References Cited

U.S. PATENT DOCUMENTS

| | | | | |
|---|---|---|---|---|
| 3,803,667 | A * | 4/1974 | Rose | A61B 17/1604 16/422 |
| 3,858,578 | A * | 1/1975 | Milo | A61B 17/02 600/229 |
| 4,143,652 | A * | 3/1979 | Meier | A61B 17/02 600/203 |
| 4,317,248 | A * | 3/1982 | Smith | B05C 17/00 15/145 |
| 4,387,478 | A * | 6/1983 | Smith | B05C 17/0205 15/145 |
| 4,547,092 | A * | 10/1985 | Vetter | A61G 7/0503 248/229.11 |
| 4,971,037 | A | 11/1990 | Pelta | |
| 5,634,620 | A * | 6/1997 | Verot | F01P 3/205 248/229.14 |
| 5,715,562 | A * | 2/1998 | Lowrey | B05C 17/022 15/144.1 |
| 6,283,912 | B1 | 9/2001 | Hu et al. | |
| 6,767,153 | B1 | 7/2004 | Holbrook | |
| 6,834,837 | B2 * | 12/2004 | Schilt | A61B 90/50 248/276.1 |
| 7,731,141 | B2 * | 6/2010 | Schuerch | A61G 13/101 248/218.4 |
| 7,770,252 | B2 * | 8/2010 | Errichiello | A46B 5/0075 15/144.1 |
| 8,216,211 | B2 * | 7/2012 | Mathis | A61B 90/57 606/1 |
| 2002/0026190 | A1 | 2/2002 | Walulik et al. | |
| 2004/0143153 | A1 | 7/2004 | Sharrow | |
| 2006/0058579 | A1 * | 3/2006 | Oberlaender | A61B 17/3462 600/102 |
| 2006/0074406 | A1 | 4/2006 | Cooper et al. | |
| 2006/0229500 | A1 * | 10/2006 | Schuerch | A61G 13/101 600/234 |
| 2008/0086150 | A1 * | 4/2008 | Mathis | A61B 90/57 606/130 |
| 2009/0036890 | A1 | 2/2009 | Karidis | |
| 2010/0183362 | A1 * | 7/2010 | Franklin | B05C 17/022 403/96 |
| 2010/0298648 | A1 | 11/2010 | Gray | |

FOREIGN PATENT DOCUMENTS

| | | |
|---|---|---|
| DE | 10209209 A1 | 2/2004 |
| DE | 102009009575 A1 | 8/2010 |
| EP | 1826301 A1 | 8/2007 |
| EP | 0862385 B1 | 12/2007 |
| EP | 1357829 B1 | 10/2010 |
| JP | 2001-517101 A | 10/2001 |
| JP | 3519328 B2 | 4/2004 |
| JP | 2006187815 A | 7/2006 |
| JP | 2009-174673 A | 8/2009 |
| JP | 3166092 U | 2/2011 |
| RU | 2463014 | 10/2012 |
| WO | 03017853 A1 | 3/2003 |

OTHER PUBLICATIONS

Japanese Office Action Notice of Reasons for Refusal as translated in English, dated Mar. 29, 2016, which issued for corresponding Japanese Patent Application No. 2015-541194, 4 pages.
Translated search report for the first Office Action for CN201380055793.0, which corresponds to this application, dated Jul. 1, 2016, 2 pages.
Translated search report for the first Office Action for CN201380056361.1, which corresponds to this application, dated Jul. 29, 2016, 2 pages.

* cited by examiner

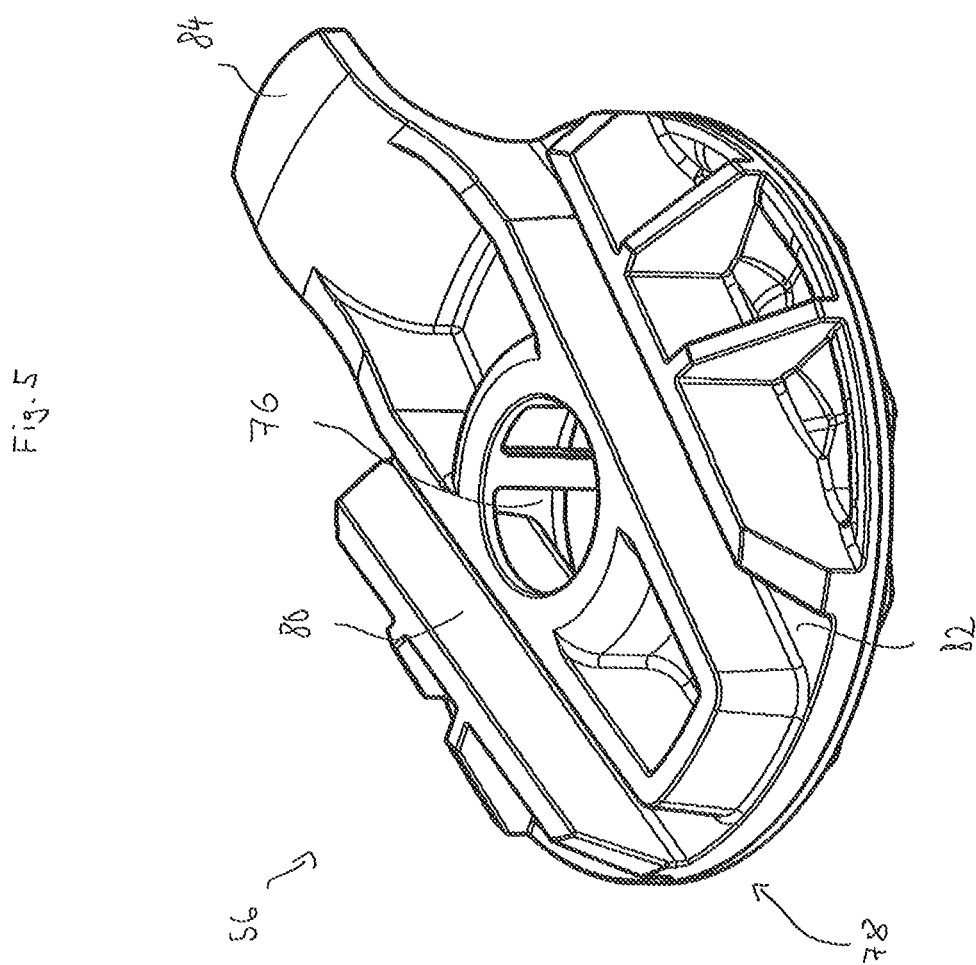

INSTRUMENT HOLDER

CROSS REFERENCE TO RELATED APPLICATIONS

This application is entitled to the benefit of and incorporates by reference subject matter disclosed in International Patent Application No. PCT/EP2013/075332 filed on Dec. 3, 2013, and German Application No. 10 2012 112 712.3 filed on Dec. 20, 2012.

TECHNICAL FIELD

The present invention relates to an instrument holder for mounting a medical instrument on a joint arm with a body, a holder for holding the medical instrument on the body and a coupling element for attaching the body to the joint arm.

BACKGROUND

Nowadays, for surgical applications increasingly assistance systems are used comprising a joint arm, which is for example attachable to the slide rail of an operating table. A medical instrument is coupled to the free end of the freely movable joint arm. For example, in laparoscopy, a rigid endoscope provided with an optical system is mounted on the joint arm and oriented such that the surgeon can see into the target region to be examined or to be treated surgically.

In addition to such an assistance system, usually further instruments are used in surgery, which the surgeon or an assistant has to operate manually. An example is a wound retractor which the assistant inserts into the wound and holds with one hand, so that the surgical area remains accessible for the surgeon. Holding the wound retractor is quite exhausting for the assistant, in particular if the wound retractor has to be held in the same position for a longer period of time.

SUMMARY

It is the object of the invention to provide a possibility for holding a medical instrument for a longer period of time in an easy and stable manner in the desired position without medical personnel being required for this.

The invention solves this object by the instrument holder comprising a body, a holder for holding the medical instrument on the body, and a coupling element for attaching the body to the joint arm, wherein the holder comprises a threaded shank provided with an external thread, which extends from a first contact surface formed on the body, a receiving disc having a through-hole, by means of which the receiving disc can be put on the threaded shank and is rotatable about the threaded shank, a second contact surface, which faces the first contact surface, when the receiving disc is put on the threaded shank, and a receiving groove, which is formed on a side of the receiving disc facing away from the second contact surface for receiving a part of the medical instrument, and a locking element provided with an internal thread, wherein the locking element covers the receiving groove at least partly, when the internal thread of said locking element engages with the external thread of the threaded shank, whereby said part of the medical instrument is held in the receiving groove and can be tightened against the receiving disc such that the two contact surfaces are force-locked relative to each other. Advantageous embodiments are indicated in the sub-claims.

The invention provides an instrument holder including a body, a coupling element for attaching the body to a joint arm and a holder for holding the medical instrument on the body. According to the invention, the holder comprises a threaded shank provided with an external thread, a receiving disc and a locking element provided with an internal thread. The threaded shank extends from a first contact surface formed on the body. The receiving disc has a through-hole by which the receiving disc can be put on the threaded shank and is rotatable about the threaded shank. The receiving disc further has a second contact surface, which faces the first contact surface, when the receiving disc is put on the threaded shank, and a receiving groove, which is formed on a side of the receiving disc facing away from the second contact surface for receiving a part of the medical instrument. The locking element covers the receiving groove at least partly, when the internal thread of said locking element engages with the external thread of the threaded shank, whereby said part of the medical instrument is held in the receiving groove and can be tightened against the receiving disc such that the two contact surfaces are force-locked relative to each other.

Thus, the instrument holder according to the invention forms a mechanical interface between the joint arm attached to the operating table and the medical instrument. For mounting the medical instrument, the instrument holder is first attached by means of its coupling element to the joint arm and subsequently the instrument is mounted to the instrument holder. For this, the receiving disc is put by means of its through-hole onto the threaded shank and subsequently the locking element is screwed onto the threaded shank. As the locking element, as soon as it is engaged with the threaded shank, at least partly covers the receiving groove, the part of the instrument being arranged in the receiving groove is fixed therein. When the locking element is screwed further onto the threaded shank, the first contact surface formed on the body of the instrument holder contacts the second contact surface formed on the receiving disc. By tightening the receiving disc with the locking element on the threaded shank, the two contact surfaces are pressed onto each other in a force-locked manner, causing the medical instrument to be fixed in the desired position. If the instrument shall be adjusted, the locking element only has to be detached a little, so that the force-locked contact of the two contact surfaces is released. In this detached state, in which the receiving disc is still engaged with the threaded shank and thus covers the instrument part arranged in the receiving groove, the instrument can be freely rotated about the threaded shank. As soon as the desired position of the instrument is adjusted, the locking element being engaged with the threaded shank is tightened against the receiving disc again.

Thus, the instrument holder according to the invention allows to position the instrument easily and reliably as desired and to fix it subsequently in the desired position. Thus, in particular, when the instrument shall be held in the same position for a longer period of time, the instrument holder facilitates handling of the instrument significantly.

The medical instrument mounted by means of the instrument holder according to the invention is preferably a wound retractor, e.g. a so-called Langenbeck wound retractor formed in one piece from a straight hook shaft and a hook blade bent at right angles.

The instrument holder is preferably produced by injection molding. Thus, for example the body of the instrument holder together with the threaded shank formed on the body, the receiving disc and the locking element can respectively be formed as one-piece plastic injection-moulded articles, which are subsequently assembled for mounting the instrument on the joint arm.

In a preferred embodiment, the receiving groove is formed from two straight partial grooves being respectively open at both groove ends, wherein the through-hole of the receiving disc is arranged between the two partial grooves. The two partial grooves allow for a particularly easy fixing of the medical instrument in the receiving disc.

Preferably, the two partial grooves are arranged such, that their extensions intersect at an acute angle, for example in a range of 10° to 30°, outside of the receiving disc.

In a particularly preferred embodiment, a nose is formed on the receiving disc, which laterally, or if the receiving disc is formed circular, radially projects from the edge of the receiving disc and is formed to hold a U-shaped portion of the medical instrument between itself and the body of the instrument holder. If the receiving groove is formed from two straight partial grooves being respectively open at both groove ends, as described above, the nose is preferably positioned in a region between the extensions of the two partial grooves. If the grooves are arranged non-parallel, the nose is preferably arranged in a region, in which the extensions of the two partial grooves diverge. This design of the receiving disc is intended for a medical instrument, wherein the instrument part thereof to be arranged in the receiving disc has a U-shaped portion with two legs, which converge starting from the base of this portion. In this case, the two legs of the U-shaped portion can just be positioned in the two partial grooves such that the base connecting the two legs is arranged outside of the nose formed on the receiving disc in the top view on the receiving disc. Subsequently, the instrument is pulled in a direction in which the two legs of the U-shaped portion converge. Thus, the base of the U-shaped portion gets in a region below the nose and is fixed in a space positioned between the nose and the body of the instrument holder on which the receiving disc is arranged. Even if the locking element is not yet screwed onto the threaded shank, it can thus be ensured that the U-shaped portion is not detached from the receiving disc.

Preferably, the locking element has a star knob by which the locking element is manually screwable onto the threaded shank. In this manner, the force-locked pressing connection between the two contact surfaces can be created and detached particularly easily in order to fix the medical instrument on the instrument holder or to pivot it in the desired position.

Preferably, the first contact surface has a first toothing and the second contact surface has a second toothing which engage, when the two contact surfaces contact each other. Due to the two engaging toothings the contact surfaces can contact each other in a rotationally fixed manner particularly reliably.

Advantageously, the two toothings respectively include a plurality of teeth arranged along a circle, which respectively have a triangular tooth profile. The circular arrangement of the teeth as well as the triangular profile thereof allows to rotate the receiving disc in a particularly easy manner on the body of the instrument holder and thus to pivot the instrument part held on the receiving disc, when the locking element is engaged with, but not tightened at the threaded shank. In this state, the two toothings slide with low friction on top of each other due to their triangular tooth profile, when the instrument is pivoted and thus the receiving disc is rotated on the body of the instrument holder.

However, this tooth profile is only an exemplary design. A wave-like profile is e.g. also possible.

Preferably, at least one first locking element is arranged in the through-hole of the receiving disc, which engages with at least one second locking element formed on the threaded shank, when the receiving disc is put on the threaded shank. For example, the first locking element is a locking pin with a locking nose directed radially inwards in the through-hole of the receiving disc, while the second locking element is a locking groove formed in annular shape on the threaded shank. In the state, in which it is put on the threaded shank, the receiving disk is held by means of the two locking elements on the threaded shank and is at the same time rotatable about it. Thus, the locking elements form a retainer.

The invention further provides a medical assistance device, comprising a joint arm, at least one medical instrument and an instrument holder of the above-described type.

Preferably, the assistance device comprises a plurality of instruments, which respectively have an identically constructed instrument part receivable in the receiving groove of the instrument holder. Thus, a plurality of instruments can be selectively coupled to the joint arm by means of the same instrument holder.

BRIEF DESCRIPTION OF THE DRAWINGS

The invention will be explained in more detail in the following on the basis of the Figures, wherein:

FIG. 5 shows an illustration of a receiving disc provided in the instrument holder.

DETAILED DESCRIPTION

Figure 1:
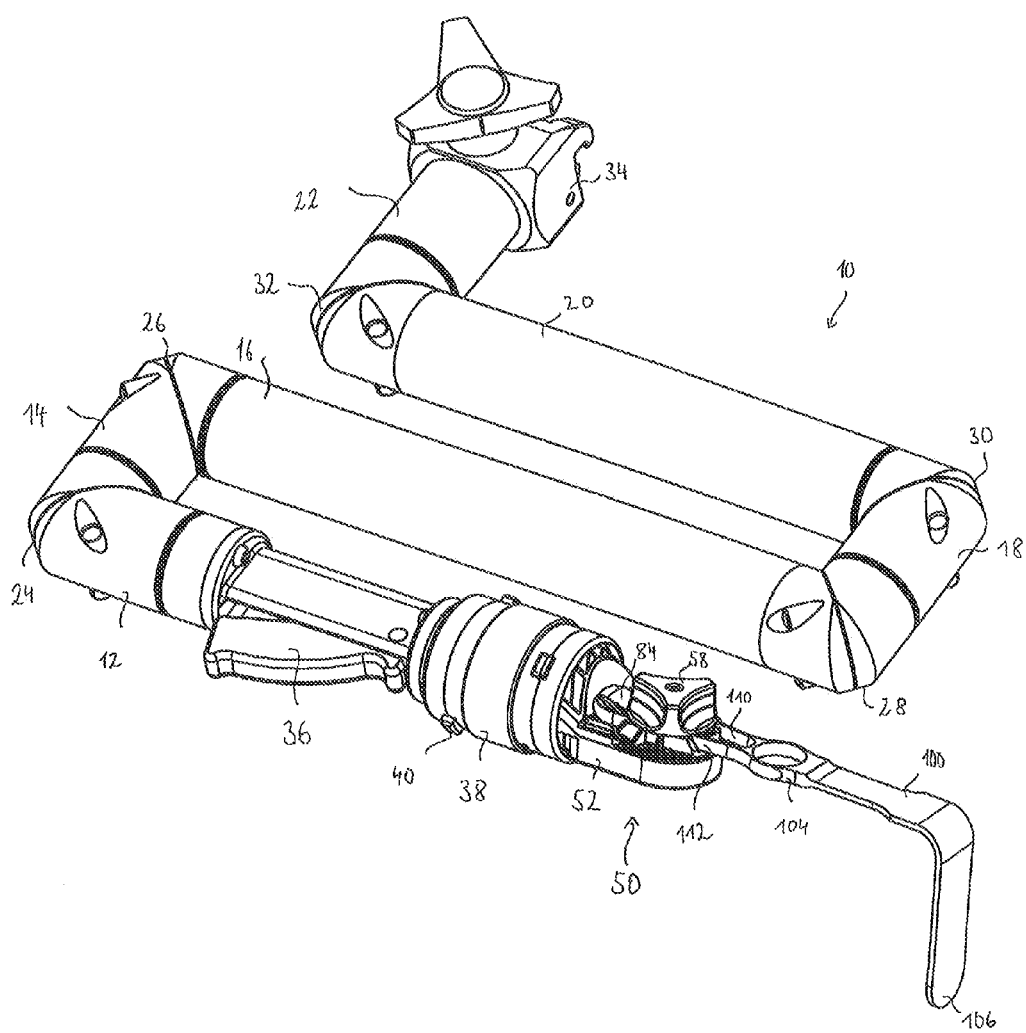
FIG. 1 shows an assistance device according to the invention with a joint arm, an instrument holder and a wound retractor mounted on the joint arm by means of the instrument holder.

FIG. 1 shows an assistance device with a joint arm 10 including a plurality of rigid holding members 12, 14, 16, 18, 20 and 22 which are coupled to each other by joints 24, 26, 28, 30 and 32. At one end of the joint arm 10 a mounting device 34 is arranged, which serves to attach the joint arm 10 to a slide rail (not shown) of an operating table. On the other end of the joint arm 10 a handle 36 is positioned, which can be manually operated by the user in order to unlock the joint arm 10.

If no operating force is exerted on the handle 36, the holding members 12, 14, 16, 18, 20 and 22 of the joint arm 10 are rigidly coupled to each other by the joints 24, 26, 28, 30 and 32. In this state, the joint arm forms a rigid unit.

If the user presses the handle 36, the holding members 12, 14, 16, 18, 20 and 22 coupled to each other by the joints 24, 26, 28, 30 and 32 become movable relative to each other by means of an unlocking mechanism being not part of the present invention and therefore not described in more detail here, so that the user can orient the joint arm 10 in space as desired. If the user subsequently releases the handle 36 again, the joints 24, 26, 28, 30 and 32 are locked and the joint arm 10 is fixed in its changed orientation.

On the end of the joint arm 10, at which the handle 36 is positioned, a quick coupling 38 is coupled to the joint arm 10. The quick coupling 38 includes a plurality of unlocking buttons 40, which are pressed in order to detach the quick coupling 38 from the joint arm 10.

By means of the quick coupling 38 a medical instrument, in the present embodiment a Langenbeck wound retractor 100, is coupleable to the joint arm 10. For this, an instrument holder, generally designated 50 in FIG. 1, is provided as intermediate piece, which is coupled to the quick coupling 38 and holds the wound retractor 100. The joint arm 10 together with the quick coupling 38, the instrument holder 50 and the wound retractor 100 thus form a device, which is attachable to the operating table and can be used for keeping the wound area accessible for the surgeon by inserting the wound retractor 100 in the wound and fix it in the desired position therein.

Figure 2:
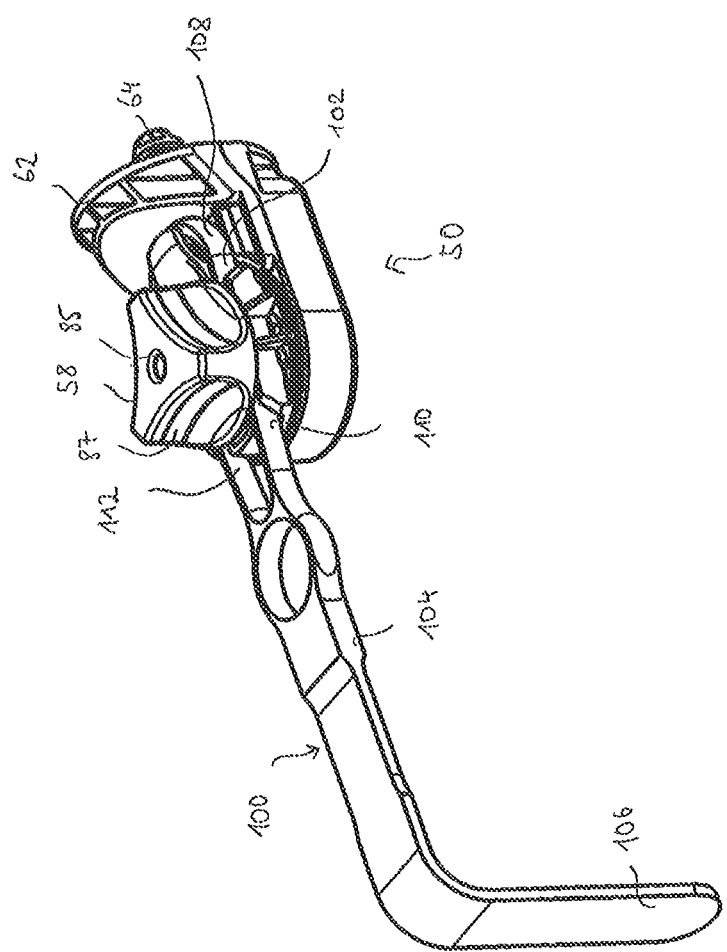
FIG. 2 shows an illustration showing the wound retractor attached to the instrument holder without joint arm.

FIG. 2 shows the instrument holder 50 with the wound retractor 100 attached thereto taken alone, i.e. without the joint arm 10 and the quick coupling 38. As shown in FIG. 2, the wound retractor 100 is a one-piece component, including a U-shaped end portion 102, a hook shank 104 adjacent to the end portion 102 as well as a hook blade 106 bent at right angles. The U-shaped portion 102 is formed from a base 108 and two legs 110 and 112 adjacent to the base 108. The legs 110 and 112 are positioned in a plane, however they are arranged non-parallel, in that they converge in said plane starting from the base 108.

Figure 3:
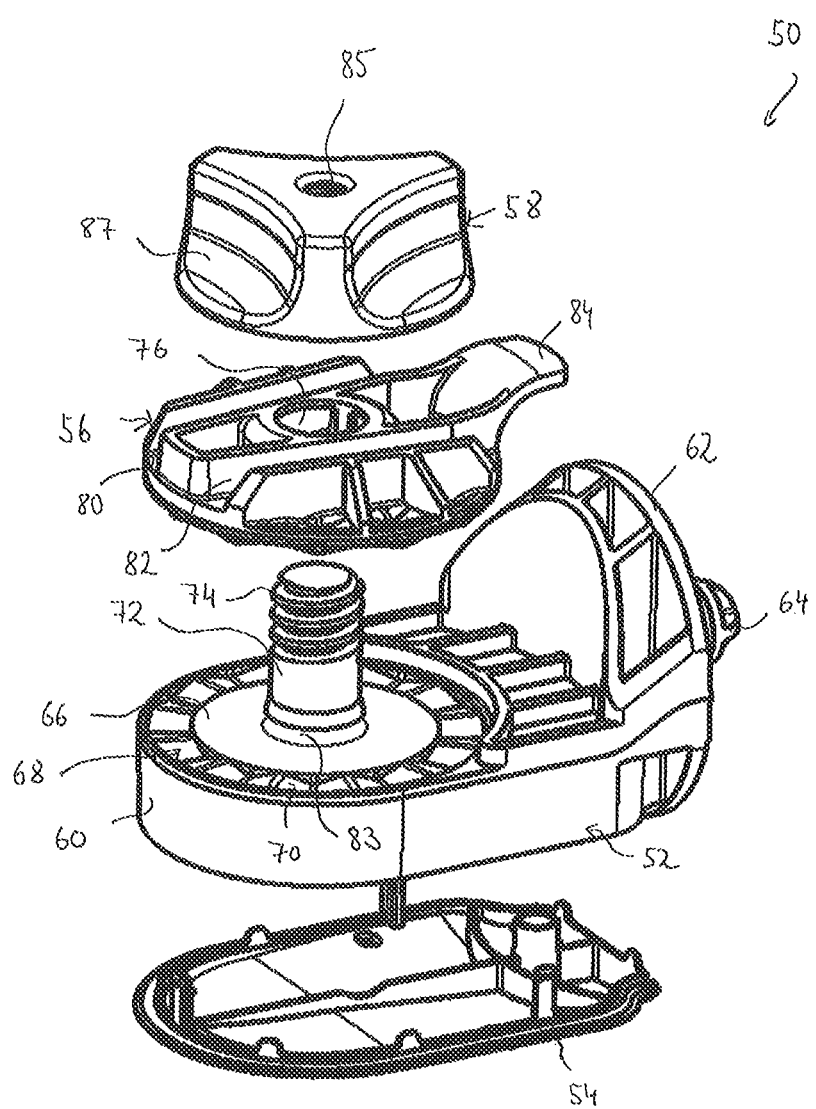
FIG. 3 shows an exploded view showing the individual components of the instrument holder.
Figure 4:
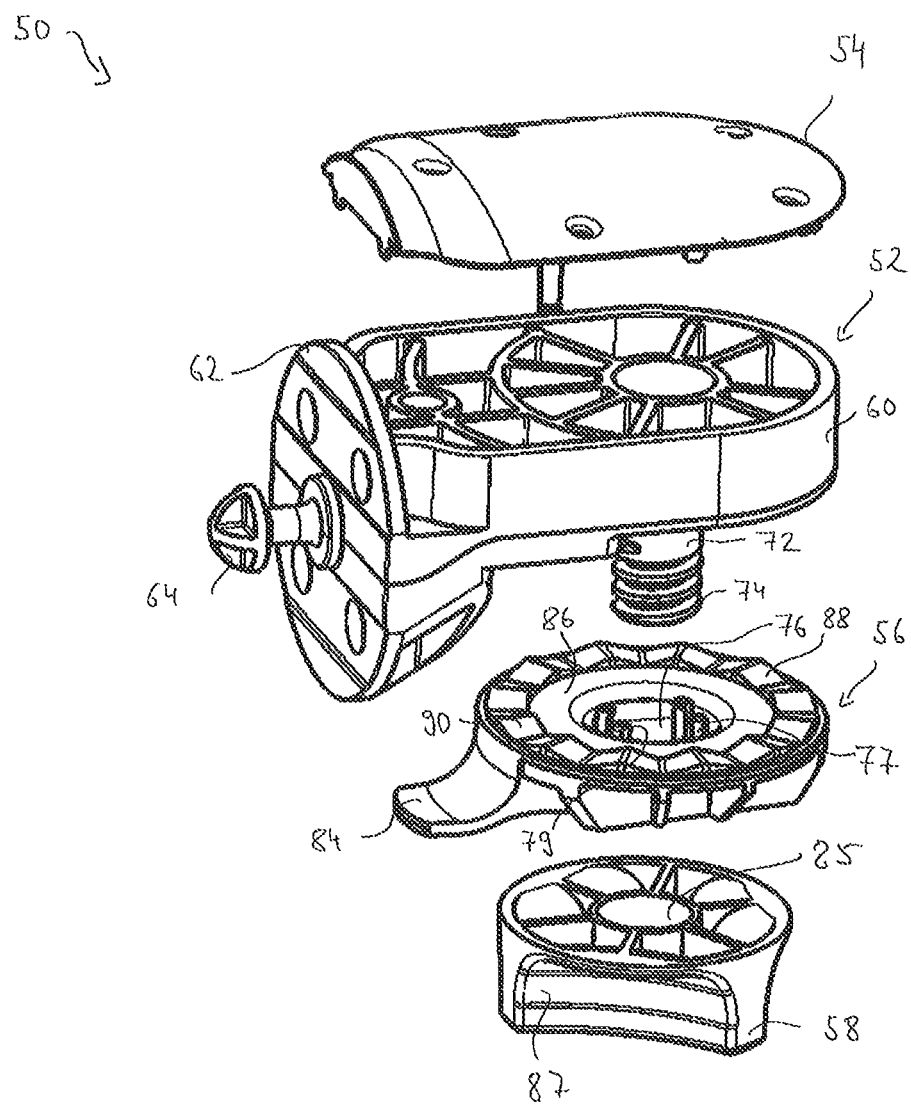
FIG. 4 shows an illustration corresponding to FIG. 3 from another perspective.

In FIGS. 3 and 4, the individual components of the instrument holder are illustrated in exploded views and different perspectives.

The instrument body consists of a body 52, a cover 54, which is put onto the bottom side of the body 52, a receiving disc 56 and a locking element 58. The body 52, the cover 54, the receiving disc 56 and the locking element 58 are respectively formed as a plastic injection-moulded article.

The body 52 includes a bottom plate 60 and a circular locking plate 62 from which a locking trunnion 64 projects. The locking trunnion 64 forms a coupling element by which the body 52 is coupled to the quick coupling 38. On the top side of the bottom plate 60 a first contact surface 66 is formed including a first circumferential toothing 68. The toothing 68 consists of a plurality (in the present embodiment twelve) teeth 70, which are arranged along a circle and respectively have a triangular tooth profile.

On the bottom plate 60 of the body 52 a threaded shank 72 is formed in the region of the first contact surface 66, which threaded shank 72 is provided with an external thread 74. The threaded shank 72 is surrounded by the circular first toothing 68.

The receiving disc 56, which is again illustrated taken alone in FIG. 5, has a centered, circular through-hole 76 by which the receiving disc 56 can be put on the threaded shank 72. In the through-hole 76, four locking pins 77 are arranged, which respectively include a locking nose 79 on their free end being directed radially inwards (cf. FIG. 4). When the receiving disc 56 is put on the threaded shank 72, the locking noses 79 engage a locking groove 83 formed close to the first contact surface 66 in an annular manner at the threaded shank 72. Thus, when it is put on the threaded shank 72, the receiving disc 56 is held close to the contact surface 66 and at the same time freely rotatable about the threaded shank 72 with a force provided due to the elastic engagement of the locking noses 79 in the locking groove 83. Thus, the locking pins 77 and the locking groove 83 serve as retainer.

As can best be seen in FIG. 5, the receiving disc 56 has a receiving groove 78 formed from two straight partial grooves 80 and 82. The partial grooves 80 and 82 are respectively open at both groove ends and formed on the receiving disc 56 such that their extensions intersect at an acute angle outside of the receiving disc 56. The orientation of the two partial grooves 80 and 82 corresponds to the orientation of the two legs 110 and 112 of the U-shaped portion of the wound retractor 100 (cf. FIG. 2). The partial grooves 80 and 82 are further arranged such that the through-hole 76 is positioned between the partial grooves 80 and 82.

Further, on the receiving disc 56 a nose 84 is formed, which projects from the circular edge of the receiving disc in a radial direction. The nose 84 is adjacent to the partial grooves 80 and 82, namely at those groove ends whose extensions diverge. As shown in FIG. 2, the nose 84 serves to receive the base 108 of the U-shaped portion 102 of the wound retractor 100 between itself and the bottom plate 60 of the body 52.

As shown in FIG. 4, the receiving disc 56 has a second contact surface 86 at its bottom side, which is intended to come in pressure contact with the first contact surface 66 formed on the top side of the bottom plate 60 of the body 52. On the second contact surface 86 of the receiving disc 56 a second circumferential toothing 88 is formed, which is formed from a plurality (in the present embodiment twelve) teeth 90. The teeth 90 are arranged along a circle surrounding the through-hole 86. Like the teeth 70 of the first toothing 68 the teeth 90 of the second toothing 88 also respectively have a triangular tooth profile. The two toothings 68 and 88 are determined to engage, when the receiving disc 56 is put on the threaded shank 72 and the two contact surfaces 66 and 86 contact each other. If the receiving disc 56 of the locking element 58 is positioned unloaded on the bottom plate 60 of the body 52, there is a specific number of stable rotational positions in which the two toothings 68 and 88 engage. This number is determined by the number of teeth 70 or 90 of the respective toothing 68 or 88.

In the present embodiment, twelve stable rotational positions are provided. The angle between two adjacent rotational positions correspondingly is 360°/12 equal 30°. Of course, these indications are only intended as examples.

The locking element 58 includes an internal thread 85 screwable onto the threaded shank 72. On the locking element 58 a star knob 87 is formed by which the user can screw the locking element 58 manually onto the threaded shank 72. The locking element 58 is formed such that it covers the two partial grooves 80 and 82 from above, when it is screwed onto the threaded shank 72. Thus, when being arranged in the partial grooves 60 and 82, the two legs 110 and 112 of the wound retractor 100 are prevented by the locking element 58 from being detached from the partial grooves 80 and 82.

In order to mount the wound retractor 100 to the instrument holder 50, first the receiving disc 56 is put on the threaded shank 72. Subsequently, the U-shaped portion 102 of the wound retractor 100 is attached to the receiving disc 56 such that the two legs 110 and 112 of the U-shaped portion 102 of the wound retractor 100 are received in the two partial grooves 80 and 82 and the base 108 of the U-shaped portion 102 is arranged below the nose 84 and thus between said nose and the bottom plate 60 of the body 52. Subsequently, the locking element 58 is screwed onto the threaded shank 72. For this, the user grasps the star knob 87 formed on the locking element 58 and tightens the locking element 58 being engaged by means of its internal thread 85 with the external thread 74 of the threaded shank 72 against the receiving disc 56. When the locking element 58 is tightened, the first contact surface 66 formed on the bottom plate 60 of the body 52 and the second contact surface 86 formed on the receiving disc 56 are positioned in a force-locked pressing contact in particular in the region of their toothings 68 and 88, so that the receiving disc 56 and thus the wound retractor 100 held therein are fixed in the desired position.

If the pivot position of the wound retractor 100 shall be changed, the user detaches the force-locked connection between the two contact surfaces 66 and 86 by detaching the locking element 58 without completely disengaging the locking element 58 and the threaded shank 72. In this state, the two toothings 68 and 88 can slide on top of each other and be brought in a new position with respect to each other. Correspondingly, the wound retractor 100 can be pivoted as desired.

In the present embodiment, the medical instrument 100 is a wound retractor. It goes without saying that the invention is not limited thereto. Thus, also instruments of another type can be coupled to the joint arm 10 with the instrument holder 50 according to the invention.

Although various embodiments of the present invention have been described and shown, the invention is not restricted thereto, but may also be embodied in other ways within the scope of the subject-matter defined in the following claims.

What is claimed is:

1. An instrument holder for mounting a medical instrument on a joint arm, comprising:
    a body,
    a coupling element for attaching the body to the joint arm,
    a threaded shank provided with an external thread, the threaded shank extending from a first contact surface formed on the body,
    a receiving disc having a through-hole, the through-hole configured to receive the threaded shank, and the receiving disc being rotatable about the threaded shank,
    the receiving disc having a second contact surface, the second contact surface facing the first contact surface when the threaded shank is received in the through-hole, and a receiving groove, which is formed on a side of the receiving disc facing away from the second contact surface for receiving a part of the medical instrument, and
    a locking element provided with an internal thread, wherein the locking element at least partly covers the receiving groove when the internal thread of said locking element engages with the external thread of the threaded shank, whereby as said locking element is tightened, said part of the medical instrument held in the receiving groove is configured to be tightened against the receiving disc and the two contact surfaces are force-locked relative to each other,
    wherein a nose formed on the receiving disc, which laterally projects from an edge of the receiving disc, is formed to hold a portion of the medical instrument between the nose formed on the receiving disc and the body.

2. The instrument holder according to claim 1, wherein the receiving groove is formed from two straight partial grooves, wherein the through-hole of the receiving disc is arranged between the two partial grooves.

3. The instrument holder according to claim 2, wherein the two partial grooves are arranged at an angle relative to each other.

4. The instrument holder according to claim 3, wherein the coupling element is a locking nose formed on the body.

5. The instrument holder according to claim 2, wherein the locking element has a knob by which the locking element is manually screwable onto the threaded shank.

6. The instrument holder according to claim 2, wherein the coupling element is a locking nose formed on the body.

7. The instrument holder according to claim 1, wherein the locking element has a knob by which the locking element is manually screwable onto the threaded shank.

8. The instrument holder according to claim 1, wherein the coupling element is a locking nose formed on the body.

9. The instrument holder according to claim 1, wherein the first contact surface has a first toothing and the second contact surface has a second toothing, which engage when the two contact surfaces contact each other.

10. The instrument holder according to claim 9, wherein the two toothings respectively include a plurality of teeth arranged along a circle, which respectively have a triangular tooth profile.

11. The instrument holder according to claim 1, wherein at least one first locking element arranged in the through-hole of the receiving disc is configured to engage with at least one second locking element formed on the threaded shank when the threaded shank is received in the through-hole of the receiving disc.

* * * * *